US010281409B2

(12) United States Patent
Yang

(10) Patent No.: US 10,281,409 B2
(45) Date of Patent: May 7, 2019

(54) INSPECTION APPARATUS AND INSPECTION METHOD USING THE SAME

(71) Applicant: LG DISPLAY CO., LTD., Seoul (KR)

(72) Inventor: Jeong-Bok Yang, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 0 days.

(21) Appl. No.: 15/650,382

(22) Filed: Jul. 14, 2017

(65) Prior Publication Data
US 2018/0188186 A1 Jul. 5, 2018

(30) Foreign Application Priority Data

Dec. 29, 2016 (KR) ........................ 10-2016-0182746

(51) Int. Cl.
G01N 21/94 (2006.01)
G01N 21/95 (2006.01)
G01B 11/06 (2006.01)
H01L 51/56 (2006.01)
H01L 51/52 (2006.01)
(Continued)

(52) U.S. Cl.
CPC ............. *G01N 21/94* (2013.01); *G01B 11/06* (2013.01); *G01N 21/8422* (2013.01); *G01N 21/8806* (2013.01); *G01N 21/95* (2013.01); *G01N 21/958* (2013.01); *G01R 31/11* (2013.01); *G01R 31/31728* (2013.01); *G09G 3/006* (2013.01); *G09G 3/3208* (2013.01); *H01L 51/0031* (2013.01); *H01L 51/50* (2013.01); *H01L 51/5253* (2013.01); *H01L 51/56* (2013.01); *G01N 2201/10* (2013.01); *G09G 2330/12* (2013.01)

(58) Field of Classification Search
CPC ........ G01N 21/64; G01N 21/94; G01N 21/95; G01N 2201/10; G01N 21/211; G01N 21/6458; H01L 21/66; H01L 51/0031; H01L 51/52; H01L 51/56; H01L 51/5253; E05F 15/431; G06K 9/00; G01B 11/06
See application file for complete search history.

(56) References Cited

U.S. PATENT DOCUMENTS

2002/0027202 A1* 3/2002 Engelhardt ........ G01N 21/6458
250/458.1
2004/0235205 A1* 11/2004 Levy .................... G01N 21/211
438/14
(Continued)

FOREIGN PATENT DOCUMENTS

KR 20090107314 A * 10/2009 ............. H01L 21/66

*Primary Examiner* — Jamil Ahmed
(74) *Attorney, Agent, or Firm* — Seed Intellectual Property Law Group LLP

(57) ABSTRACT

An inspection method includes: irradiating light through a prism to an inspection object; scanning an inspection region of the inspection object using a photographing unit; receiving, by the photographing unit, reflected light that is reflected from the inspection object; converting the reflected light received by the photographing unit into an intensity of light; and detecting a defect of the inspection object by comparing a thickness of the inspection object corresponding to the intensity of the light with a predetermined thickness of the inspection object. Therefore, the encapsulation layer is inspected before post-processes of cells or the module process, such that the yield and productivity of the OLED device can be improved.

21 Claims, 7 Drawing Sheets

(51) Int. Cl.

| | |
|---|---|
| *H01L 51/00* | (2006.01) |
| *G01R 31/11* | (2006.01) |
| *G01R 31/317* | (2006.01) |
| *G09G 3/00* | (2006.01) |
| *G09G 3/3208* | (2016.01) |
| *H01L 51/50* | (2006.01) |
| *G01N 21/84* | (2006.01) |
| *G01N 21/88* | (2006.01) |
| *G01N 21/958* | (2006.01) |

(56) References Cited

U.S. PATENT DOCUMENTS

| | | | |
|---|---|---|---|
| 2005/0276449 A1* | 12/2005 | Pedemas | E05F 15/431 382/104 |
| 2011/0207244 A1* | 8/2011 | Sung | G09G 3/006 438/7 |
| 2015/0050756 A1* | 2/2015 | Choi | H01L 51/5253 438/16 |

* cited by examiner

INSPECTION APPARATUS AND INSPECTION METHOD USING THE SAME

CROSS-REFERENCE TO RELATED APPLICATIONS

This application claims the priority of Korean Patent Application No. 10-2016-0182746 filed on Dec. 29, 2016, in the Korean Intellectual Property Office, the disclosure of which is incorporated herein by reference.

BACKGROUND

Technical Field

The present disclosure relates to an inspection apparatus and an inspection method, and in detail, to an inspection apparatus and an inspection method for inspecting a defect in an encapsulation layer included in an organic light-emitting display apparatus.

Description of the Related Art

As the era of information technology has begun, the field of display that represents electrical information signals graphically has been rapidly growing. In accordance with this, various display devices which are thinner, lighter and consume less power have been developed.

Such display devices include a liquid crystal display (LCD) device, a plasma display panel (PDP) device, a field emission display (FED) device, and an organic light emitting display (OLED) device, etc.

In detail, OLED devices have advantages over other display devices in that they are self-luminous and that they have faster response speed, higher luminous efficiency, brighter luminance and wider viewing angle. Accordingly, OLED devices are attracting attention. In addition, an OLED device capable of emitting white light has been recently developed, such that OLED devices have a wide range of applications such as backlight and illumination. Accordingly, OLED devices are recognized as one of the most important display devices.

SUMMARY

An organic light-emitting display (OLED) device includes an anode, a cathode, and an organic light emitting diode including an emissive layer (EML) disposed between the anode and the cathode. Holes in the anode are injected into the emissive layer, and electrons in the cathode are injected into the emissive layer, such that the electrons and the holes are recombined to form excitons in the emissive layer, and light is emitted therefrom.

In an OLED device including an emissive layer formed of an organic material, the OLED device is encapsulated with glass, metal or film to prevent moisture or oxygen from permeating. By doing so, oxidation of the emissive layer and the electrodes can be prevented, and the OLED device can be protected from mechanical or physical impact externally applied. Therefore, the encapsulation of the OLED device is very important because moisture or oxygen from the outside affects the lifespan or efficiency of the organic light emitting diode.

To encapsulate the organic light emitting diode, a process of forming an encapsulation layer on a mother substrate is performed, where the organic light emitting diode is formed in each of a plurality of cells for forming a plurality of panels. After forming the encapsulation layer on the mother substrate, a scribing process is carried out for cutting the mother substrate into cells.

There is a problem that the encapsulation layer cannot be formed at a desired area due to foreign matters generated during the process of forming the encapsulation layer for sealing the organic light emitting diode. If there is a defect in the encapsulation layer, a crack is created when a flexible OLED device is bent. As a result, moisture or oxygen permeates into the organic light emitting diode, such that the efficiency or the lifespan of the organic light emitting diode is deteriorated. Since the encapsulation layer is inspected during a lighting test performed after the mother substrate has been cut, there is a problem in that the yield of the OLED devices is lowered.

As mentioned above, the encapsulation layer protects the OLED device, and thus it is important to keep or maintain the encapsulation layer from being damaged. Therefore, it is important to keep or maintain the encapsulation layer from being damaged not only in the process of forming it but also in the subsequent processes.

In view of the above, the inventors of the disclosure have invented an inspection apparatus that can inspect defects in an encapsulation after forming it, and an inspection method using the same.

An aspect of the present disclosure is to provide an inspection method and an inspection apparatus capable of inspecting the whole substrate including the encapsulation layer and inspecting defects in the encapsulation layer in real-time.

And, another aspect of the present disclosure is to provide an inspection apparatus and an inspection method capable of inspecting the whole substrate without increasing the processing time.

It should be noted that objects of the present disclosure are not limited to the above-described objects, and other objects of the present disclosure will be apparent to those skilled in the art from the following descriptions.

According to an aspect of the present disclosure, there is provided an inspection method, comprising: irradiating light through a prism to an inspection object; scanning an inspection region of the inspection object using a photographing unit; receiving, by the photographing unit, reflected light that is reflected from the inspection object; converting the reflected light received by the photographing unit into an intensity of light; and detecting a defect of the inspection object by comparing a thickness of the inspection object corresponding to the intensity of the light with a predetermined thickness of the inspection object.

According to another aspect of the present disclosure, there is provided an inspection apparatus comprising: an optical inspection unit including a prism configured to separate light emitted from a light source into spectra; a mirror configured to reflect the separated light toward an inspection object; a photographing unit configured to receive a reflected light that is reflected from the inspection object and to convert the reflected light into an intensity of light; and a detection unit configured to detect a defect of the inspection object by comparing a thickness of the inspection object corresponding to the intensity of the light with a predetermined thickness of the inspection object.

The embodiments of the present disclosure will be described in the detail description with reference to the accompanying drawings.

According to an embodiment of the present disclosure, it is possible to easily detect a defect reflected by variations in the thickness of an encapsulation layer by detecting a defect in the encapsulation layer with a thickness in accordance with the intensity of the light.

According to an embodiment of the present disclosure, it is possible to detect a defect in an encapsulation layer based on the thickness of the encapsulation layer according to the intensity of the light, such that a defect in the encapsulation layer formed of a transparent film can be quantified.

And, according to an embodiment of the present disclosure, the yield and productivity of OLED device can be improved by inspecting the encapsulation layer before post-processes of cells or the module process.

And, according to an embodiment of the present disclosure, the inspection apparatus may further include a line scan camera that includes a photographing unit, such that the entire substrate including the encapsulation layer can be scanned and a defect in the encapsulation layer can be detected.

According to an embodiment of the present disclosure, the step of detecting defects in the inspection object can be performed while scanning a new inspection region, so that the inspection time can be shortened.

And, according to an embodiment of the present disclosure, the inspection apparatus can inspect the entire substrate without increasing the processing time.

It should be noted that effects of the present disclosure are not limited to those described above and other effects of the present disclosure will be apparent to those skilled in the art from the following descriptions.

The Summary is not necessarily to specify essential features of the appended claims, and thus the scope of the claims is not limited thereby.

BRIEF DESCRIPTION OF THE SEVERAL VIEWS OF THE DRAWINGS

The above and other aspects, features and other advantages of the embodiments of present disclosure will be more clearly understood from the following detailed description taken in conjunction with the accompanying drawings, in which.

DETAILED DESCRIPTION

Figure 1:
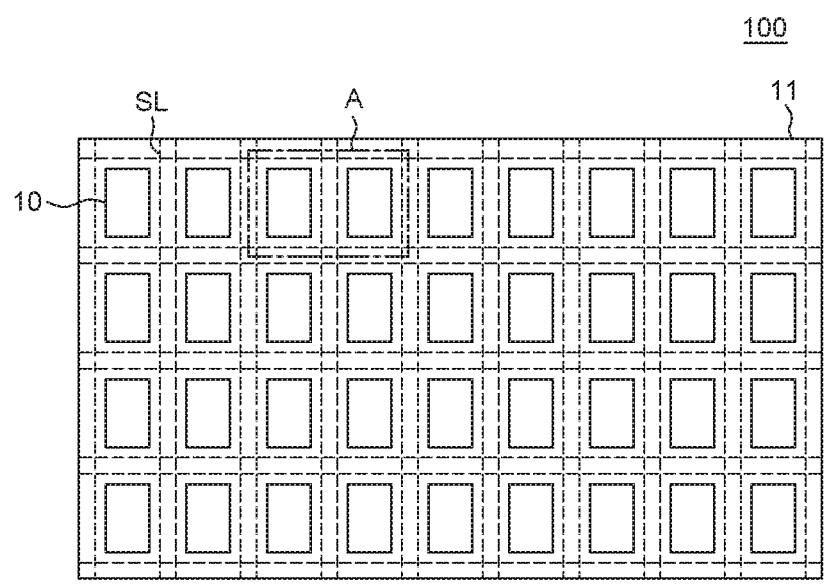
FIG. 1 is a plan view showing a mother substrate according to one or more embodiments of the present disclosure.

Advantages and features of the embodiment of present disclosure and methods to achieve them will become apparent from the descriptions hereinbelow with reference to the accompanying drawings. However, the present disclosure is not limited to embodiments disclosed herein but may be implemented in various different ways. The embodiments are provided for making the disclosure thorough and for fully conveying the scope of the present disclosure to those skilled in the art. It is to be noted that the scope of the present disclosure is defined only by the claims.

The figures, dimensions, ratios, angles, the numbers of elements given in the drawings are merely illustrative and are not limiting. Like reference numerals denote like elements throughout the descriptions. Further, in describing the present disclosure, descriptions on well-known technologies may be omitted in order not to unnecessarily obscure the gist of the present disclosure. It is to be noticed that the terms "comprising," "having," "including" and so on, used in the description and claims, should not be interpreted as being restricted to the means listed thereafter unless specifically stated otherwise. Where an indefinite or definite article is used when referring to a singular noun, e.g., "a," "an," "the," this includes a plural of that noun unless specifically stated otherwise.

In describing elements, they are interpreted as including error margins even without including explicit statements to that effect.

In describing positional relationship, such as "an element A on an element B," "an element A above an element B," "an element A below an element B" and "an element A next to an element B," another element C may be disposed between the elements A and B unless otherwise specified, for example, where the term "directly" or "immediately" is explicitly used.

In describing temporal relationship, terms such as "after," "subsequent to," "next to" and "before" are not limited to "directly after," "directly subsequent to," "immediately next to" "immediately before," and so on, unless otherwise specified.

The terms first, second, third and the like in the descriptions and in the claims are used for distinguishing between similar elements and not necessarily for describing a sequential or chronological order. These terms are used to merely distinguish one element from another. Accordingly, as used herein, a first element may be a second element within the technical idea of the present disclosure.

Features of various embodiments of the present disclosure may be combined partially or totally. As will be clearly appreciated by those skilled in the art, technically various interactions and operations are possible. Various embodiments can be practiced individually or in combination.

Hereinafter, an inspection apparatus and an inspection method using the same according to embodiments of the present disclosure will be described with reference to the accompanying drawings. In the following description, a mother substrate having a plurality of cells to form organic light-emitting panels will be described as an embodiment of an inspection object.

FIG. 1 is a view showing a mother substrate according to an embodiment of the present disclosure.

Referring to FIG. 1, a mother substrate 100 includes a plurality of cells 10 each corresponding to the respective organic light-emitting panels. That is, the plurality of cells 10 is cut into individual cells, to form a plurality of organic light-emitting panels or OLED apparatuses. The "mother substrate" 100 refers to the entire device or apparatus shown in FIG. 1 before cutting the plurality of cells 10 into individual cells, and includes a substrate 11, as well as the cells 10 which are formed on the substrate 11.

Although the cells 10 are shown as having a rectangular shape in FIG. 1, this is merely illustrative. The cells 10 may have a variety of shapes such as a circular shape. Scribing lines SL for separating the cells 10 from one another are formed around each of the cells 10. The scribing lines SL may be actually drawn on the substrate 11 or virtual scribing lines SL may be defined by alignment keys or any marks around the cells 10.

In the display area of each of the cells 10, a pixel driver circuit and an organic light emitting diode are disposed. The pixel driver circuit may include a thin-film transistor (TFT), a capacitor, etc. The organic light emitting diode includes an anode, an organic emissive layer, and a cathode.

Hereinafter, the cells 10, and the positions of an encapsulation layer in each of the cells 10 and scribing lines SL will be described in detail.

Figure 2:
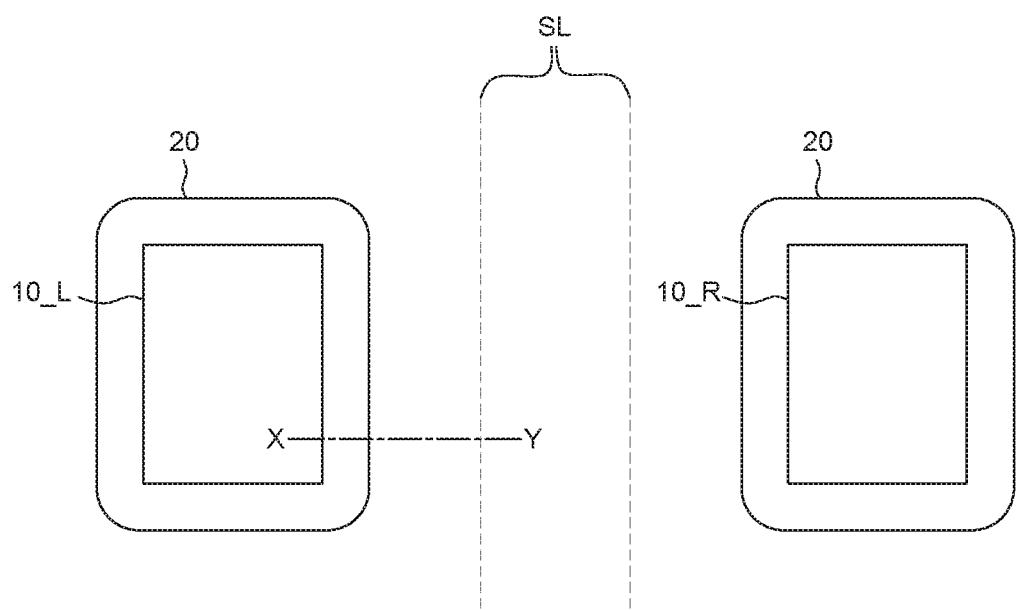
FIG. 2 is an enlarged view of area A shown in FIG. 1.

FIG. 2 is an enlarged view of area A shown in FIG. 1. Area A includes two cells 10_L and 10_R.

Referring to FIG. 2, the first cell 10_L and the second cell 10_R are shown with a scribing line SL therebetween. Each of the first cell 10_L and the second cell 10_R may be referred to as a display area.

In each of the first cell 10_L and the second cell 10_R, a pixel driving circuit and an organic light emitting diode are formed on the substrate 11. In order to protect the pixel driving circuit and the organic light emitting diode, the encapsulation layer 20 is disposed so as to surround each of the first cell 10_L and the second cell 10_R. The scribing line SL is defined between the first cell 10_L and the second cell 10_R. After forming the encapsulation layer 20 on the substrate 11, the substrate 11 may be diced along the scribing line SL.

Figure 3:
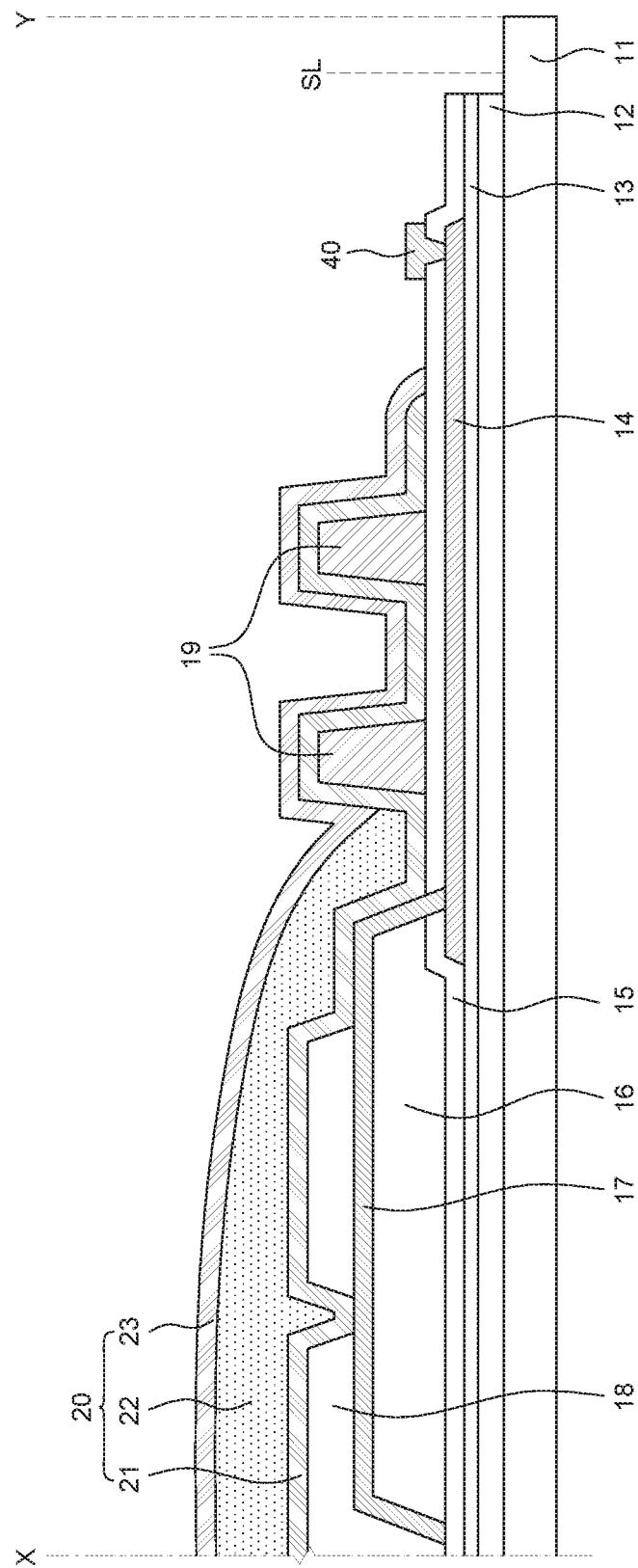
FIG. 3 is a cross-sectional view taken along line X-Y of FIG. 2.

FIG. 3 is a cross-sectional view taken along line X-Y of FIG. 2. Descriptions will be made with reference to FIG. 3 in conjunction with FIG. 2.

The substrate 11 is formed of an insulative material to support various components of the OLED device. In addition, the substrate 11 may be formed of a material having flexibility such as glass or plastic. For example, the flexible material may include polyimide (PI), polyetherimide (PEI), polyethyelene terephthalate (PET), polycarbonate (PC), polymethylmethacrylate (PMMA), polystyrene (PS), styrene-acrylonitrile copolymer (SAN), silicon-acryl resin, etc. In addition, when the organic light emitting diode that is easy to implement in a flexible display device is applied to automotive lighting or automotive display devices, design freedom is increased to allow for a variety of designs in accordance with the structure or the exterior of the automobile.

And, the OLED device according to embodiments of the present disclosure may be applied to a variety of display devices including a TV, a mobile device, a tablet PC, a monitor, a laptop computer, an automotive display device, etc. And, the OLED device may also be applied to a wearable display device, a foldable display device, a rollable display device, a bendable display device, etc. And, if the substrate 11 is a flexible substrate, the OLED device may be applied to a curved display device, a foldable display device, a rollable display device, a bendable display device, an automotive display device, etc.

A buffer layer 12 is formed on the substrate 11 to protect various components of the OLED device from the permeation of moisture ($H_2O$) or oxygen ($O_2$) from the outside of the substrate 11. The buffer layer 12 may be formed of, but is not limited to, silicon oxide (SiOx), silicon nitride (SiNx), or multiple layers thereof.

The buffer layer 12 may include a first buffer layer and/or a second buffer layer. The first buffer layer may delay diffusion of moisture and/or oxygen permeating into the substrate 11, and may be a multi-buffer. The first buffer layer may be formed of a single layer of silicon oxide (SiOx) or silicon nitride (SiNx), or multiple layers of silicon oxide (SiOx) and silicon nitride (SiNx) stacked alternately. Alternatively, the first buffer layer may be formed of multiple layers having silicon nitride (SiNx), silicon oxide (SiOx) and silicon oxynitride (SiOxNx). The second buffer layer can protect the active layer of the thin-film transistor and suppress various kinds of defects. The second buffer layer may be an active-buffer. The second buffer layer may be formed of amorphous silicon (a-Si), etc. The buffer layer 12 may include both the first buffer layer and the second buffer layer or may include one of the first buffer layer and the second buffer layer. The buffer layer 12 may be determined depending on the type and material of the substrate 11, the type of the thin-film transistor to be applied to the OLED device, etc., and may be omitted in some implementations.

A first insulating layer 13 is disposed on the buffer layer 12. Since the first insulating layer 13 may be formed on a gate electrode disposed on the buffer layer 12, it may also be referred to as a gate insulating film.

A source and drain electrode 14 is disposed on the first insulating layer 13. The source and drain electrode 14 may be formed of one of molybdenum (Mo), aluminum (Al), chromium (Cr), gold (Au), titanium (Ti), nickel (Ni), neodymium (Nd) and copper (Cu), an alloy of two or more thereof, or a multi-layer thereof. The source and drain electrode 14 may be used as a connection electrode for transmitting a voltage applied from the outside through a pad unit 40 to the pixel driving circuit disposed in the cell 10. For example, it may be, but is not limited to, a high-potential voltage (VDD), a low-potential voltage (VSS), or a data voltage (Vdata). When the connection electrode is a low-potential voltage line, the source and drain electrode 14 may be electrically connected to the cathode included in the organic light emitting diode in the non-display area.

The pad 40 may be, but is not limited to, formed of the same material as the anode 17 via the same process. The pad 40 may come in contact with the source and drain electrode 14 through a contact hole in a second insulating layer 15 on the source and drain electrode 14. A driver-IC, a flexible printed circuit board (FPCB), a chip on plastic (COP), or a chip on film (COF) may be attached to the pad 40.

The second insulating layer 15 is disposed on the source and drain electrode 14. The first insulating layer 13 and the second insulating layer 15 may be extended from the display area formed in the cell 10.

The first insulating layer 13 and the second insulating layer 15 may be formed of a single layer of silicon nitride (SiNx), silicon oxide (SiOx), or silicon oxynitride (SiOxNx). Alternatively, the first insulating layer 13 and the second insulating layer 15 may be formed of multiple layers of silicon nitride (SiNx), silicon oxide (SiOx) and silicon oxynitride (SiOxNx).

On the second insulating layer 15, a planarization layer 16 is disposed, which planarizes steps created by the thin-film transistor, etc., formed in the cell 10. The planarization layer 16 may be formed of, but is not limited to, one of acrylic resin, epoxy resin, phenol resin, polyamide resin, polyimide resin, unsaturated polyester resin, polyphenylene resin, polyphenylene sulfide resin, and benzocyclobutene.

An anode 17 is disposed on the planarizing layer 16. The anode 17 may be in contact with the source and drain electrode 14 through a contact hole in the second insulating layer 15. The anode 17 may also be used as a connection electrode for transmitting a voltage applied from the outside through the pad unit 40 to the inside of the cell 10. For example, it may be, but is not limited to, a high-potential voltage (VDD), a low-potential voltage (VSS), or a data voltage (Vdata).

A bank 18 is disposed on the anode 17 formed in the cell 10. The bank 18 may be formed of, but is not limited to, polyimide, acryl resin or benzocyclobutene (BCB) resin. And, an organic emissive layer is disposed on the bank 18 and on the portion of the anode 17 not covered by the bank 18. The cathode is disposed on the organic emissive layer and the bank 18.

A spacer may be disposed on the bank 18. The spacer can prevent damage to the organic light emitting diode that may occur by a fine metal mask (FMM) used during the process of patterning the organic emissive layer included in the emission unit of the organic light emitting diode.

The bank 18 is formed on the part of the anode 17 formed outside the cell 10, and the encapsulation layer 20 is disposed on the bank 18 so that the cell 10 is sealed. The encapsulation layer 20 includes a first encapsulation layer 21, a second encapsulation layer 22, and a third encapsulation layer 23. The encapsulation layer 20 may be composed of at least two encapsulation layers, and the number of the encapsulation layers 20 is not limited.

The first encapsulation layer 21 and the third encapsulation layer 23 may be formed of an inorganic material. For example, the first encapsulation layer 21 and the third encapsulation layer 23 may be formed of, but is not limited to, one or more layers of silicon oxide (SiOx), silicon nitride (SiNx), and silicon oxynitride (SiOxNy). And, the first encapsulation layer 21 and the third encapsulation layer 23 may be formed by, but is not limited to, chemical vapor deposition (CVD) or atomic layer deposition (ALD).

At least one encapsulation layer formed of an inorganic material may be further disposed on the third encapsulation layer 23. For example, the inorganic material may be formed of, but is not limited to, one or more layers of silicon oxide (SiOx), silicon nitride (SiNx), and silicon oxynitride (SiOxNy).

The second encapsulation layer 22 can prevent problems resulting from foreign material or particles that may be generated during the processes. Accordingly, the second encapsulation layer 22 may be a particle cover layer (PCL). For example, if the third encapsulation layer 23 formed of an inorganic material is disposed on the surface of the first encapsulation layer 21 where particles are attached, without the second encapsulation layer 22, there may be a gap around the particles since the inorganic material does not have strong adhesive force with the particles on the surface of the first encapsulation layer 21. Accordingly, the encapsulation layer 20 may be peeled off due to this gap. Accordingly, when the first encapsulation layer 21 is defective due to cracks generated by the foreign matter or the particles, the foreign matter or the particles can be covered by the second encapsulation layer 22. That is, the second encapsulation layer 22 formed of an organic material is disposed between the first encapsulation layer 21 and the third encapsulation layer 23, such that it is possible to prevent the encapsulation layer 20 from being peeled off by covering the particles and the periphery of the particles.

The second encapsulation layer 22 may be formed of an organic material and may be formed as a transparent film. For example, the second encapsulation layer 22 may be formed of, but is not limited to, one of silicon oxycarbide (SiOCz), acrylic resin, and epoxy resin.

The second encapsulation layer 22 may be formed by, but is not limited to, screen printing or inkjet printing. The inkjet printing is a technique in which droplets of a material are discharged via a nozzle of an inkjet head, and the material is dispensed and coated onto the second encapsulation layer 22. By forming the second encapsulation layer 22 by the inkjet printing, the thickness of the second encapsulation layer 22 can be reduced compared to that formed by the screen printing. Therefore, when the encapsulating layer is formed by the ink-jet printing, the encapsulating layer becomes thinner, which is advantageous for the implementation of a foldable display device, a bendable display device, or a rollable display device. And, it is easy to control the position of the second encapsulation layer 22 at the time of forming it, which is advantageous for implementation of a narrow bezel.

When the second encapsulation layer 22 is formed by the inkjet printing, the material that is used has a viscosity that is similar to that of water, such that it easily flows. Thus, a dam 19 may be disposed around the cell 10 to limit the forming region in the second encapsulation layer 22. The dam 19 can suppress the overflow of the second encapsulation layer 22. The dam 19 may have a single structure or a double structure depending on the height by which the second encapsulation layer 22 is applied and the height of the dam 19. The dam 19 may be formed of the same material as one or more insulating patterns formed in the display area. For example, the dam 19 may be formed of the same material as the bank 18. The dam 19 may be, but is not limited to, formed as a double layer of the same material as the bank 18 and the spacer. Although two dams 19 are shown in FIG. 3, the number of the dams is not limited to two. For example, one or more dams may be formed and is not limited the numbers of the dams.

It is desired to increase the height of the second encapsulation layer 22 to prevent the foreign matter from being peeled off. However, as the height of the second encapsulation layer 22 increases, the number of the dam 19 or the height of the dam 19 also has to be increased. And, if it fails to adjust the amount of the organic material to applied to form the second encapsulation layer 22, the organic material flows over the dam 19 to invade the scribing line SL, the pad portion 40, or the bending area. Accordingly, it is necessary to detect the overflow of the second encapsulation layer 22.

And, when the organic light-emitting panel formed by cutting the substrate into the cells 10 is used for a foldable display device, a bendable display device or a rollable display device, there is a bending area where a part of the organic light-emitting panel is bent or folded. When a defect is created in the encapsulation layer 20 in the bending area, cracks are generated in the encapsulation layer 20 in the process of bending or folding a part of the organic light-emitting panel. Defects or cracks in the encapsulation layer 20 may provide a path via which moisture or oxygen permeates into the organic light-emitting panel.

And, when a plurality of touch electrodes is formed on the encapsulation layer 20 in order to configure a touch functionality, there arises a problem that a short-circuit is formed between the touch electrodes due to a defect in the encapsulation layer 20.

And, when the second encapsulation layer 22 is formed by the inkjet printing, the first encapsulation layer 21 may fail to be completely covered by the second encapsulation layer 22 if a nozzle is clogged or the ink is not sufficiently spread out. In this case, it may be determined that the second encapsulation layer 22 was not applied or insufficiently applied. Accordingly, it is necessary to detect a defect caused when the second encapsulation layer 22 formed of a transparent film is not applied or insufficiently applied.

Additionally, defects that may occur when the second encapsulation layer 22 is formed by the ink-jet printing include, for example, defects due to particles, defective formation of the encapsulation layer due to poor spreading of the ink, defects due to insufficient or excessive application of the second encapsulation layer 22 caused by increase or decrease in the amount of the ink discharged from a nozzle, defects caused when the second encapsulation layer 22 is not applied or insufficiently applied due to the clogging of an inkjet, defects caused by variations in the curing conditions for curing the second encapsulation layer 22, defects due to the overflow of the second encapsulation layer 22, etc. These defects result in irregularities having a variety of shapes including linear or circular shape on the second encapsulation layer 22.

Since there is no inspection method or inspection apparatus for detecting the above-described defects in the second encapsulation layer 22 yet, such defects in the second encapsulation layer were detected after post-processes of cells or a module process, which are processes of inspecting panels after cutting the substrate into the cells. This results in decrease in the yield or productivity of the OLED devices. Moreover, if the second encapsulation layer 22 is inspected after the module process by human naked eyes, it is difficult to detect a minute defect in the second encapsulation layer 22 which is a transparent film. In addition, the skill, experience and concentration of the operator affect the inspection results of the OLED device, and thus the inspection results by human naked eyes may not be reliable. Further, since the inspection by human naked eyes is carried out manually, it takes a long time to conduct the inspection of OLED devices, such that the yield or productivity of the OLED devices decreases.

Therefore, in order to improve the efficiency, lifespan, reliability, yield and productivity of the OLED device, it is very important to detect defects in the encapsulation layer 20 before post-processes of cells or a module process. Further a method for inspecting defects in a transparent film is required, which is difficult to detect by human naked eyes or by typical vision techniques. Under the circumstances, an inspection apparatus and an inspection method capable of detecting defects in the encapsulation layer 20 and detecting defects in the transparent film before post-processes of cells or a module process will be described with reference to FIGS. 4 to 7.

Figure 4:
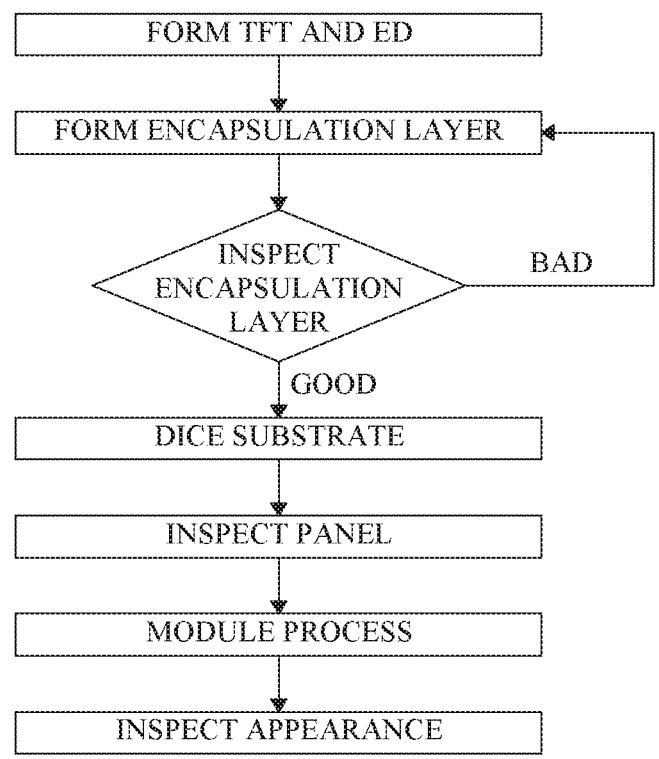
FIG. 4 is a flowchart illustrating a manufacturing and inspection procedure of an organic light-emitting panel according to embodiments of the present disclosure.

FIG. 4 is a flowchart for illustrating the manufacturing and inspection procedure of an organic light-emitting panel according to one or more embodiments of the present disclosure. The manufacturing process of organic light-emitting panels will be described with reference to FIGS. 1 to 3, and an inspection method according to the manufacturing process of organic light-emitting panels will be described.

In the display area of each of the cells 10 included in the substrate 11, a pixel driver circuit and an organic light emitting diode (ED) are formed. The pixel driver circuit may include a thin-film transistor (TFT), a capacitor, etc. The organic light emitting diode includes an anode, an organic emissive layer, and a cathode. The organic emissive layer may emit red, green or blue light, and may be formed using an organic light emitting material that is a phosphorescent material or fluorescent material. Alternatively, the emissive layer may include quantum dots (QDs).

Then, an encapsulation layer 20 is formed on the organic light emitting diode to seal the cell 10. At this time, the encapsulation layer 20 may be a single layer or a multilayer formed of two or more layers.

Then, after the encapsulation layer is formed on the organic light emitting diode, it is inspected whether there is a defect in the encapsulation layer. The encapsulation layer may include all of the first encapsulation layer, the second encapsulation layer and the third encapsulation layer. The third encapsulation layer may be omitted.

After the encapsulation layer 20 is formed, the second encapsulation layer among the encapsulation layer 20 is inspected to detect whether there is a defect. The second encapsulation layer 22 is inspected among other layers because the second encapsulation layer 22 frequently causes a defect due to the thickness difference. However, this is merely illustrative. The first encapsulation layer and the third encapsulation layer may also be inspected.

If it is determined that there is a defect in the encapsulation layer 20, the process feedbacks to the process of forming the encapsulation layer 20 to remove or solve the defect in the encapsulation layer 20. Therefore, the inspection is carried out immediately after the encapsulation layer 20 is formed, such that a feedback signal is sent to the processing equipment used in forming the encapsulation layer 20 as soon as a defect in the encapsulation layer 20 is detected. Accordingly, it is possible to solve the defect in the encapsulation layer 20 to improve the yield. In addition, it is possible to prevent defects that may occur in subsequent panel inspection or visual inspection, thereby reducing the processing cost.

If it is determined that the encapsulation layer 20 is good after the inspection, a barrier film may be further disposed on the encapsulation layer 20. The barrier film may be a polarizing plate having polarizing function. The barrier film may be omitted.

Then, the step of cutting the substrate 11 is performed. The substrate 11 is cut along the scribing lines SL into a plurality of organic light-emitting panels. Each of the organic light-emitting panels separated from the substrate 11 may be a minimum unit capable of working as a display device.

Then, an electric signal is applied to the organic light-emitting panel to perform panel inspection for detecting defective images such as spot or point defects, line defects, etc. If the step of inspecting the encapsulation layer 20 after the formation of the encapsulation layer 20 is not performed, a defect is detected in the step of inspecting the organic light-emitting panels. As used herein, the step of forming the encapsulation layer 20 may be referred to as a pre-process of cells, while the steps of cutting the substrate after forming the encapsulation layer 20 and inspecting the panels may be referred to as post-processes.

After the panel inspection is completed, the module process is carried out. The module process improves image quality by attaching an optical film, a printed circuit board and a driver-IC to the organic light-emitting panels, and applies an external signal to the organic light-emitting panels to drive respective organic emitting diodes.

After the module process is completed, the organic light-emitting panels are subjected to exterior visual inspection step. The visual inspection is a process of determining whether the components are properly attached during the module process. The visual inspection may include overall image inspect of the organic light-emitting panels and reliability check which may occur after aging. If there is a defect in the encapsulation layer 20, the image and reliability defects due to defect or cracks in the encapsulation layer 20 can be detected in the visual inspection.

Therefore, by detecting a defect in the encapsulation layer 20 after forming the encapsulation layer 20 and before the post-processes of cells or before the module process, a feedback signal can be sent in real-time to the processing equipment that forms the encapsulation layer 20. Accordingly, it is possible to check out a defect during the panel inspection or the visual inspection to reduce the cost and to improve the yield or productivity.

Next, an inspection apparatus capable of detecting a defect in the encapsulation layer 20 will be described.

Figure 5:
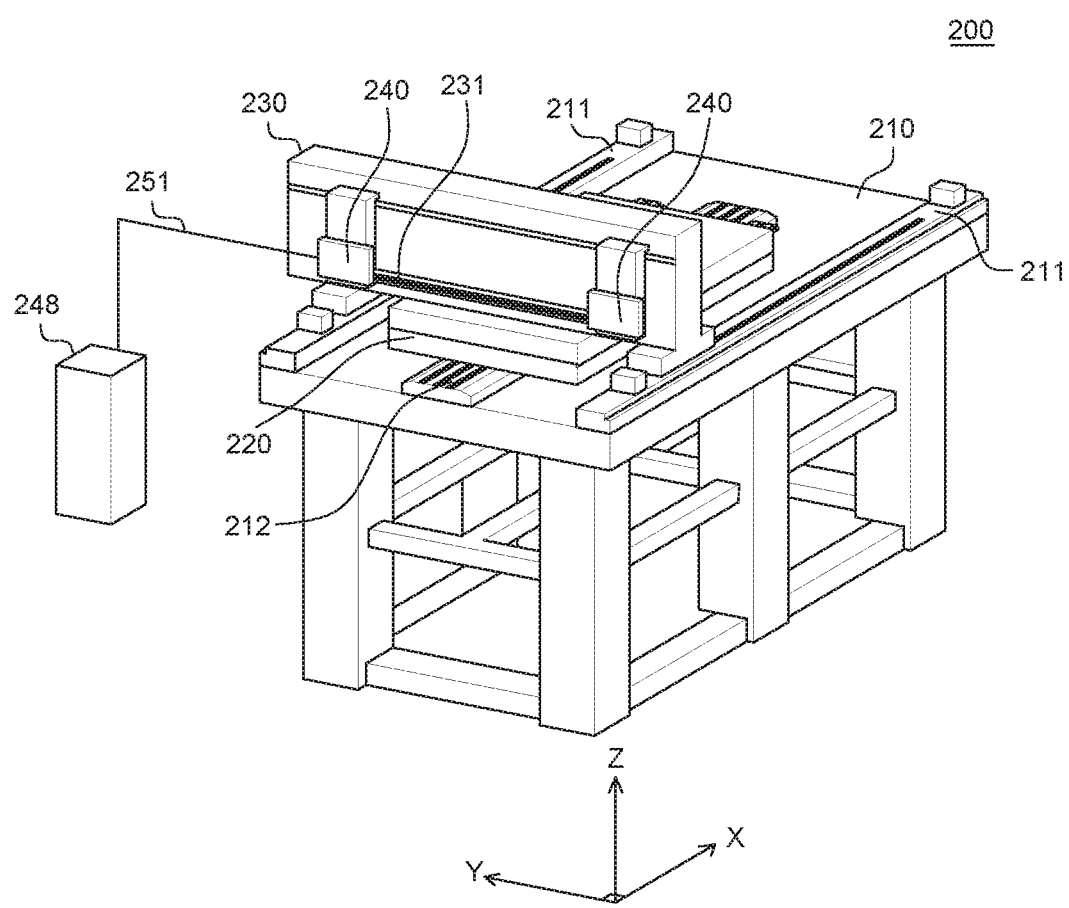
FIG. 5 is a perspective view showing an inspection apparatus according to embodiments of the present disclosure.

FIG. 5 is a view showing an inspection apparatus according to embodiments of the present disclosure.

FIG. 5 is an inspection apparatus for inspecting an inspection object for a defect in the encapsulation layer. The mother substrate 100 shown in FIG. 1 will be described as an example of the inspection object.

The inspection apparatus 200 may include a stage 210, an x-axis moving rail 211 for moving an optical inspection unit 240 in the x-axis direction, a holder 220 for holding an inspection object, and a holder moving rail 212 for moving the holder 220 in the x-axis direction.

A horizontal structure 230 for mounting the optical inspection unit 240 is disposed on the moving rail 211. The horizontal structure 230 may include a y-axis moving rail 231 by which the optical inspection unit 240 is movable in the y-axis direction. The horizontal structure 230 may also be referred to as a gantry. The horizontal structure 230 can move in the x-axis, the y-axis and the z-axis directions along with the inspection object. A driving unit for moving the horizontal structure 230 in the x-axis, y-axis and z-axis directions is disposed below the horizontal structure 230. For example, the driving unit may be, but is not limited to, a linear motor.

A plurality of optical inspection units 240 may be used to inspect scan areas of the inspection object part by part, thereby saving the inspection time of the inspection object, i.e., the encapsulation layer. Three or more optical inspection units 240 may be provided.

In order to suppress the influence by the external environment on the optical inspection unit 240 during the inspection, a chamber of a nitrogen ($N_2$) atmosphere, which is a glove box, may be installed to accommodate the inspection apparatus 200.

The optical inspection unit 240 can move the inspection object on the x-axis and the y-axis as desired by the y-axis moving rail 231 and inspect a defect in the encapsulation layer included in the inspection object. The data measured by the optical inspection unit 240 is transmitted to a detection unit 248 through an optical cable 251 connected to the optical inspection unit 240. The detection unit 248 may include an image processor that extracts an image of the subject and compares the thickness of the inspection object received from the optical inspection unit 240 with a predetermined thickness of the inspection object, and a determiner that determines whether there is a defect based on the difference in the thickness. Further, the detection unit 248 may include a display unit that displays determination results. The display unit may be, for example, a computer.

In addition, the inspection apparatus 200 may include an alignment camera mounted on the horizontal structure 230 so that it senses an alignment mark on an inspection object or a substrate when the inspection object is placed on the holder 220, and aligns the optical inspection unit 240 with the inspection object while moving the holder 220 in the y-axis direction and a theta (θ) direction. And, a driving unit for moving the holder 220 in the y-axis direction and the theta (θ) direction is disposed below the holder 220. For example, the driving unit may be, but is not limited to, a linear motor.

The inspection apparatus 200 may include an auto focusing unit mounted on the horizontal structure 230 so that it can adjust the focus on the inspection object in real-time, which can be changed while the optical inspection unit 240 moves along with the inspection object, by adjusting the distance to the inspection object.

As described earlier, the encapsulation layer 20 may be formed of a silicon-based material or a polymer material and may be a transparent film. It is difficult to check the transparent film by human naked eyes, and it is difficult to check the existence of the transparent film even with general inspection apparatus. Therefore, the optical inspection unit 240 is used for detecting a defect in the transparent film.

Figure 6:
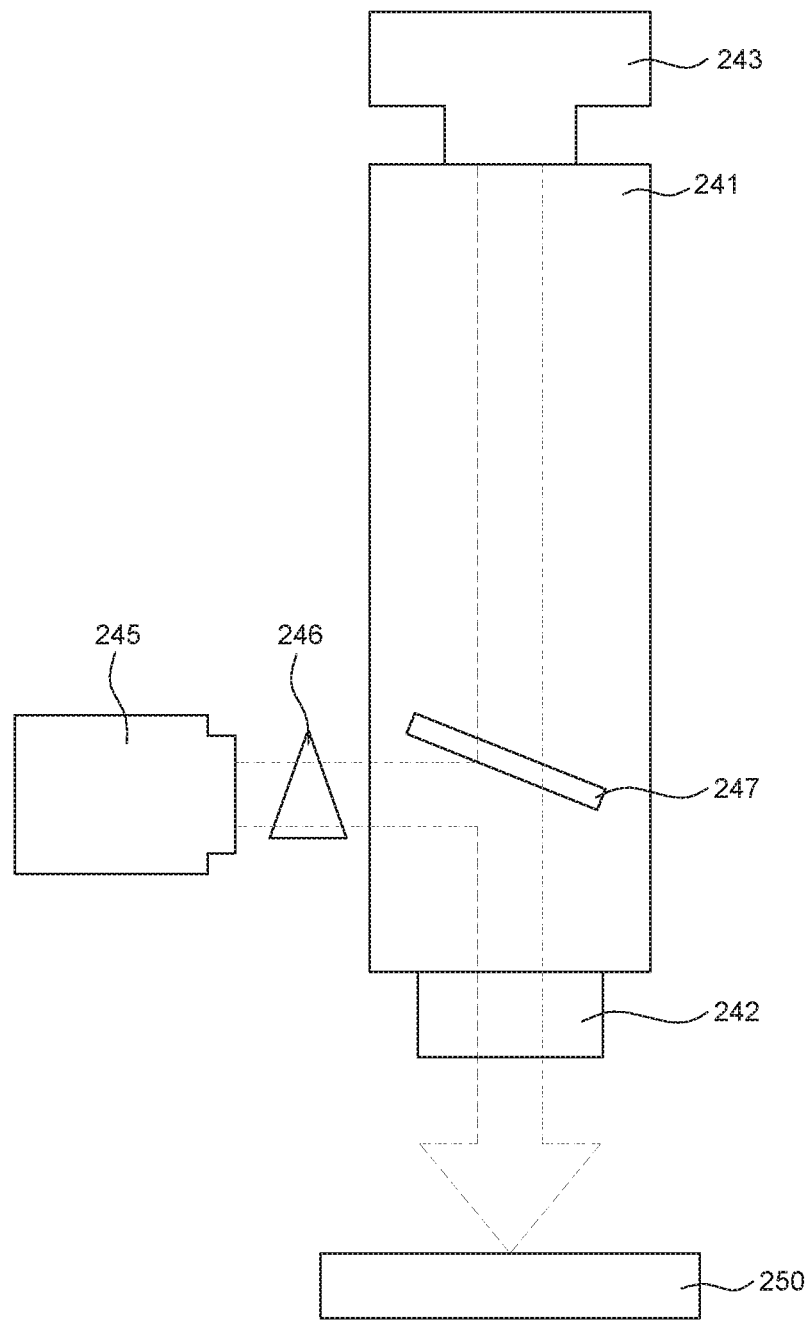
FIG. 6 is a side view showing an optical inspection unit according to embodiments of the present disclosure.
Figure 7:
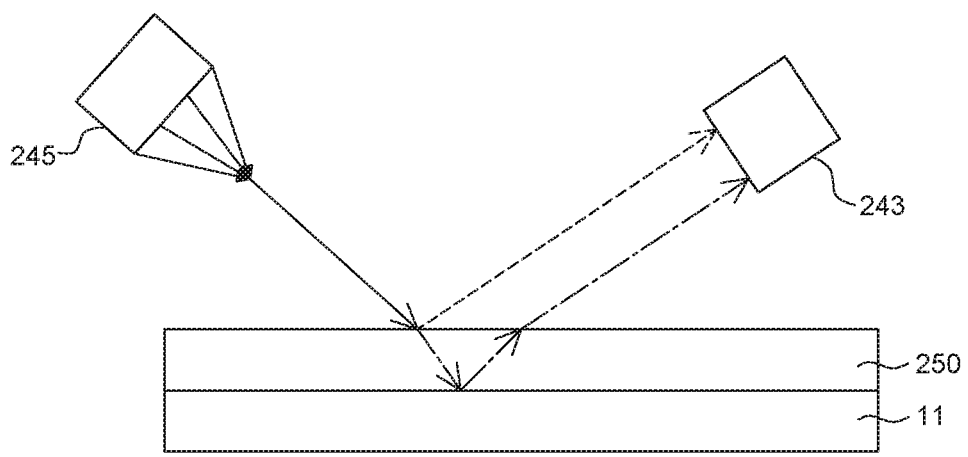
FIG. 7 is a side view illustrating a method for detecting a defect in an inspection object according to embodiments of the present disclosure.

FIG. 6 is a view showing an optical inspection unit according to embodiments of the present disclosure. FIG. 7 is a view for illustrating a method for detecting a defect in an inspection object according to embodiments of the present disclosure. The inspection apparatus and the inspection method will be described in conjunction with FIGS. 1 and 2.

The optical inspection unit 240 included in the inspection apparatus 200 includes a light source 245, a lens barrel 241, and a photographing unit 243.

The photographing unit 243 may be a line scan camera. The line scan camera can scan the area of 50 mm by 1,500 mm at a time and can observe the inspection object 250 while it moves. Accordingly, it can inspect every cell 10 along the periphery to check or determine a defect in the inspection object. Therefore, the entire substrate can be inspected by the line scan camera which is the photographing unit 243, and thus a defect in the encapsulation layers, i.e., the inspection objects 250 included in the entire substrate can be inspected. Since it may take a long time to inspect every cell on the mother substrate 100, a plurality of optical inspection units 240 may be used to inspect the inspection objects 250 on the mother substrate 100 by dividing them into groups in order to reduce the process time. Therefore, the inspection apparatus according to one or more embodiments of the present disclosure can inspect the entire substrate without increasing the processing time.

The line scan camera, which is the photographing unit 243, displays a color image. Therefore, it has an advantage in that it can easily detect defects in case the inspection object 250 is formed as or includes a transparent film.

The lens barrel 241 may include at least one lens or a filter. The filter may be a bandpass filter for splitting light from the light source 245 by wavelengths. The light from the light source 245 can be divided into lights in different wavelengths by the bandpass filter. For example, the lights in wavelengths corresponding to red, green, blue and infrared rays, respectively, can be produced. And, the at least one lens included in the lens barrel 241 may be a magnification lens and a condenser lens or a collecting lens for condensing the light, etc. For example, a magnification lens may include a high magnification lens.

The wavelength of the light from the light source 245 may be a wavelength of visible light to infrared light, and may range from 400 nm to 900 nm. The light source 245 can increase the range of the wavelength so as to include the visible light and the infrared light and may use infrared rays for the inspection object which is out of range of the visible light, thereby improving the visibility. More than one light source 245 may be provided. The plurality of light sources may be red, green, blue, and white light sources, respectively.

And, a prism 246, a mirror 247 and a lens 242 are added to the optical inspection unit 240 to detect a defect in the encapsulation layer, which is a transparent film. This will be described with reference to FIGS. 1, 2 and 5.

Referring to FIG. 6, the light from the light source 245 is transmitted to the prism 246.

The angle of incidence of the light from the light source 245 may range from 10 degrees to 90 degrees from the horizontal plane of the inspection object 250. The light source 245 may further include a tilt unit, which is an angle adjusting unit, to adjust the angle of incidence of the light. Alternatively, the angle adjusting unit of the light source 245 may be used to adjust different reflection angles for different materials of the inspection object 250.

The light source 245 may be disposed on both sides of the lens barrel 241. In case that one of the two light sources 245 is out of order, the other one can be used. Each of the two light sources 245 includes a tilt unit which is an angle adjusting unit.

The prism 246 separates light from the light source 245 into spectra. In this case, the range of the wavelength of light can be increased by the prism 246. When a beam splitter is used instead of the prism 246, there may arise a problem that a portion of light from the light source 245 is reflected and the other is transmitted, and thus the amount of incident light on the inspection object 250 is reduced, such that wavelength range becomes smaller.

The light split by the prism 246 is reflected by the mirror 247. The mirror 247 may be a half-mirror (or half transparent and half reflecting mirror). The half-mirror exhibits the property of transmitting half of incident light and reflecting half of the incident light. The mirror 247 may further include a tilt unit, which is an angle adjusting unit, to increase the intensity of light irradiated from the light source 245 onto the inspection object 250.

The light is reflected by the mirror 247 toward the inspection object 250. That is, the light from the light source 245 passes through the prism 246 and is reflected by the mirror 247 toward the inspection object 250. The inspection object 250 is the mother substrate 100, and in more detail, it may be the encapsulation layer 20 formed in each cell 10 on the mother substrate 100.

The light reflected by the inspection object 250 passes through the lens barrel 241 and is transmitted to the photographing unit 243. The photographing unit 243 scans the inspection object 250 and receives the reflected light to convert the reflective light into the intensity of the light.

Referring to FIG. 5, the detection unit 248 extracts an image of the inspection object 250, and compares a predetermined thickness of the inspection object 250 with the thickness of the inspection object 250 according to the intensity of the light, thereby detecting if there is a defect in the inspection object 250. The detection unit 248 extracts images of the inspection object 250 received from the photographing unit 243 for each of the wavelengths corresponding to red, green and blue. Then, the detection unit 248 converts the intensity of the light of the inspection object 250 received from the photographing unit 243 into the thickness of the inspection object 250. If there is a defect in the inspection object 250, the intensity of the light becomes larger than the predetermined intensity of the light of the inspection object 250, and accordingly there is a difference in thickness of the inspection object 250. In this case, the predetermined thickness of the inspection object is obtained by manufacturing at least five samples, acquiring the intensity of light for each of the samples, and then acquiring the thicknesses according to the intensities of the light. The thickness according to the intensity of the light should be available in any area of the inspection object 250. In the detection unit 248, the thickness in association with the predetermined intensity of the light of the inspection object may be stored.

The lens 242 may be disposed on or under the mirror 247. The lenses 242 disposed under the mirror 247 may have the number of pixels corresponding to the number of pixels of the line scan camera which is the photographing unit 243. For example, if the number of pixels of the line scan camera is 4,000, the lenses are configured to provide corresponding to the 4,000 pixels. In this case, the lens 242 may be referred to as a 4K lens. When the lens 242 and the line scan camera, which is the photographing unit 243, are combined together, the visibility of the image of the inspection object 250 can be improved.

The lens 242 may also be disposed above the mirror 247. That is, when the lens 242 is disposed in the lens barrel 241, no additional lens should be disposed in the lens barrel 241. When the lens 242 is disposed in the lens barrel 241, the lens barrel 241 serves to connect the lens 242 to the photographing unit 243, and the lens 242 in the lens barrel 241 serves to transmit light having passed through the mirror 247 to the photographing unit 243.

An auxiliary camera may be further disposed around the light source 245. The auxiliary camera may be for monitoring the thickness of the inspection object 250 not for inspecting the inspection object 250.

Accordingly, the optical inspection unit 240 according to the embodiment of the present disclosure separates the light into spectra by the prism 246, increases the reflectance of the inspection object 250 at a plurality of wavelengths, and increases the intensity of the light by the mirror 247. Accordingly, the thickness of the transparent film, i.e., the inspection object 250 can be measured, so that the defect in the inspection object 250 can be easily detected. The visibility of the image of the inspection object 250 can be improved by the lens 242 disposed above or below the mirror 247.

By providing the photographing unit 243 included in the optical inspection unit 240, it is possible to detect defects in the entire substrate on which the encapsulation layer is formed. Then, by converting the thickness of the encapsulation layer, which is the inspection object 250, into the thickness according to the intensity of the light, it is possible to quantify the defect of the transparent film when the inspection object 250 is a transparent film.

A method of detecting a defect in an inspection object will be described with reference to FIGS. 6 and 7.

Referring to FIG. 7, red, green, blue and white light from the light sources 245, illuminate the inspection object 250 on the substrate 11.

Referring to FIG. 6, the light from the light sources 245 is reflected by the mirror 247 toward the inspection object 250. The reflective light reflected from the inspection object 250 passes through the mirror 247 again and is transmitted to the photographing unit. In FIG. 7, the dotted line represents the surface reflection, and the one-dot chain line represents the interface reflection. When the light is reflected from the inspection object 250, the surface reflection and the interface reflection are synthesized, such that the intensity of the light of the inspection object 250 is changed. The photographing unit 243 converts the reflective light reflected from the inspection object 250 into the intensity of the light while scanning the inspection object 250.

When the inspection object 250 is scanned using light, light is continuously reflected from the inspection object 250. The photographing unit 243 collects light continuously reflected from the inspection object 250 and continuously outputs a photocurrent. The intensity of the photocurrent varies in proportion to the intensity of the light. Therefore, a change in the intensity of the light can be known from a change in the photocurrent. The light is differently reflected from the inspection object 250 depending on the characteristics of the encapsulation layer, which is the inspection object 250, and the intensity of the light changes depending on a defect in the encapsulation layer. By detecting the intensity of the light of the inspection object 250 and detecting the thickness of the inspection object 250 according to the light intensity by using the method, it is possible to efficiently inspect whether there is a defect in the encapsulation layer.

When a defect in the inspection object 250 is inspected by the above-described method, the time taken for detecting a defect in the inspection object 250 may be equal to the time taken for scanning the inspection object 250. This is because the detecting unit 248 detects a defect in the inspection object 250 during the scanning time of the inspection object 250. In detail, the optical inspection unit 240 scans along the inspection area of the inspection object 250 once in the x-axis or the y-axis direction. Subsequently, during the scanning along the next inspection region, a process of comparing the data of the previously scanned inspection area with the data stored in the detection unit 248 and analyzing datum are performed, to determine whether there is a defect. Therefore, the inspection time of the inspection object 250 can be reduced.

According to an embodiment of the present disclosure, it is possible to efficiently detect a defect when the inspection object 250 is a transparent film by detecting a defect in the encapsulation layer which is the inspection object 250 with the thickness according to the intensity of the light.

And, according to an embodiment of the present disclosure, when the encapsulation layer, which is the inspection object 250, is formed by ink-jet printing, it is possible to detect a defect that may occur when the encapsulation layer is not applied or insufficiently applied on the substrate. By doing so, a defect in the encapsulation layer can be detected in advance, before the post-processes of the cell or the module process. Therefore, the yield and productivity of the OLED device can be improved.

According to an embodiment of the present disclosure, it is possible to detect a defect due to variations in the thickness of an encapsulation layer by detecting a defect in the encapsulation layer with a thickness converted in accordance with the intensity of the light. That is, if the encapsulation layer is formed by ink-jet printing, it is possible to detect defects due to particles, defects caused when the encapsulation layer is not applied or insufficiently applied due to the clogging of a nozzle of an inkjet, defective formation of the encapsulation layer due to poor spreading of the ink, defects due to insufficient or excessive application of the encapsulation layer caused by increase or decrease in the amount of the ink discharged from a nozzle, defects caused by variations in the curing conditions for curing the encapsulation layer, defects due to the overflow of the encapsulation layer, etc.

According to an embodiment of the present disclosure, the step of detecting defects in the inspection object can be performed while scanning a new inspection area, so that the inspection time can be shortened.

The embodiments of the present disclosure can also be described as follows:

According to an embodiment of the present disclosure, an inspection method comprises irradiating light through a prism to an inspection object; scanning an inspection region of the inspection object using a photographing unit; receiving, by the photographing unit, reflected light that is reflected from the inspection object; converting the reflected light received by the photographing unit into an intensity of light; and detecting a defect of the inspection object by comparing a thickness of the inspection object corresponding to the intensity of the light with a predetermined thickness of the inspection object. Therefore, the encapsulation layer is inspected before post-processes of cells or the module process, such that the yield and productivity of the OLED device or apparatus can be improved.

The method may further include separating the light from a light source into spectra by the prism; reflecting the separated light toward the inspection object by a mirror; and passing the reflected light from the inspection object through the mirror.

The wavelength of the light from the light source may be within a range from 400 nm to 900 nm.

The mirror may include a half-mirror.

The photographing unit may include a line scan camera.

The detecting a defect of the inspection object may be performed while a different inspection region of the inspection object is scanned.

The inspection object may include an encapsulation layer of an organic light-emitting panel.

The inspection object may include a transparent film of an organic light-emitting panel.

The inspection method may be implemented prior to post-processes of the organic light-emitting panel.

The irradiating light to the inspection object may further include irradiating the light through a lens disposed above or below the mirror.

According to an aspect of the present disclosure, an inspecting apparatus comprises an optical inspection unit including a prism configured to separate light emitted from a light source into spectra; a mirror configured to reflect the separated light toward an inspection object; a photographing unit configured to receive a reflected light that is reflected from the inspection object and to convert the reflected light into an intensity of light; and a detection unit configured to detect a defect of the inspection object by comparing a thickness of the inspection object corresponding to the intensity of the light with a predetermined thickness of the inspection object. Accordingly, it is possible to easily detect a defect in an inspection object with the thickness according to the intensity of the light irradiated onto the inspection object.

The wavelength of the light emitted from the light source may be within a range from 400 nm to 900 nm.

The mirror may include a half-mirror.

The mirror may include an angle adjusting unit

The inspection object may include an encapsulation layer of an organic light-emitting panel.

The encapsulation layer may include a particle cover layer.

The inspection object may include a transparent film of an organic light-emitting panel.

The photographing unit may include a line scan camera and display a color image.

The apparatus may further include an alignment camera configured to align the inspection object with the optical inspection unit.

The apparatus may further include an auto focusing unit configured to adjust focus of the optical inspection unit with respect to the inspection object when the optical inspection unit moves along an inspection region of the inspection object.

The apparatus may further include a lens having a pixel number corresponding to a number of pixels of the photographing unit.

The detection unit may convert the intensity of the light into the thickness of the inspection object corresponding to the intensity of the light.

The inspection apparatus may be disposed prior to a device for post-processes of the organic light-emitting panel.

Thus far, embodiments of the present disclosure have been described in detail with reference to the accompanying drawings. However, the present disclosure is not limited to the embodiments, and modifications and variations can be made thereto without departing from the technical idea of the present disclosure. Accordingly, the embodiments disclosed in the present disclosure and the accompanying drawings are used not to limit but to describe the spirit of the present disclosure. The scope of the present disclosure is not limited only to the embodiments and the accompanying drawings. Therefore, it should be understood that the above-described embodiments are not limiting but illustrative in all aspects. The scope of protection sought by the present disclosure is defined solely by the appended claims and all equivalents thereof are construed to be within the true scope of the present disclosure.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An inspection method, comprising:
   positioning an organic light-emitting panel on a holder, the holder being movable along a first axis;
   irradiating light through a prism of an optical inspection assembly to an encapsulation layer of the organic light-emitting panel, the optical inspection assembly being attached to a gantry positioned over the holder, the gantry being movable along the first axis, the optical inspection assembly being movable along a second axis that is perpendicular to the first axis;
   scanning an inspection region of the encapsulation layer by moving the optical inspection assembly along the first axis and the second axis;
   receiving, by a camera of the optical inspection assembly, reflected light that is reflected from the encapsulation layer;
   converting the reflected light received by the camera into an intensity of light;
   comparing a thickness of the encapsulation layer corresponding to the intensity of the light with a predetermined thickness of the encapsulation layer; and
   detecting a defect of the encapsulation layer based on the comparing the thickness of the encapsulation layer corresponding to the intensity of the light with the predetermined thickness of the encapsulation layer,
   wherein the encapsulation layer is a transparent film.

2. The method of claim 1, further comprising:
   separating the light from a light source into spectra by the prism;
   reflecting the separated light toward the encapsulation layer by a mirror; and
   passing the reflected light from the encapsulation layer through the mirror.

3. The method of claim 2, wherein a wavelength of the light from the light source is within a range from 400 nm to 900 nm.

4. The method of claim 2, wherein the mirror includes a half-mirror.

5. The method of claim 1, wherein the camera comprises a line scan camera.

6. The method of claim 1, wherein the detecting a defect of the encapsulation layer is performed while a different inspection region of the encapsulation layer is scanned.

7. The method of claim 1, wherein the inspection method is implemented prior to post-processes of the organic light-emitting panel.

8. The method of claim 2, wherein the irradiating light to the encapsulation layer further includes irradiating the light through a lens above or below the mirror.

9. An inspection apparatus, comprising:
   a holder configured to hold an organic light-emitting panel, the holder being movable along a first axis;
   a gantry positioned over the holder and the organic light-emitting panel, the gantry movable along the first axis;
   an optical inspection assembly attached to the gantry and movable along a second axis that is perpendicular to the first axis, the optical inspection assembly including:
     a prism configured to separate light emitted from a light source into spectra;
     a mirror configured to reflect the separated light toward an encapsulation layer of the organic light-emitting panel, the encapsulation layer including an organic material; and
     a camera configured to receive a reflected light that is reflected from the encapsulation layer, and to convert the reflected light into an intensity of light; and
   a defect detector communicatively coupled to the optical inspection assembly, the defect detector configured to compare a thickness of the encapsulation layer corresponding to the intensity of the light with a predetermined thickness of the encapsulation layer, and to detect a defect of the encapsulation layer based on the comparison,
   wherein the encapsulation layer is a transparent film.

10. The apparatus of claim 9, wherein a wavelength of the light emitted from the light source is within a range from 400 nm to 900 nm.

11. The apparatus of claim 9, wherein the mirror includes a half-mirror.

12. The apparatus of claim 9, wherein the mirror includes an angle adjuster.

13. The apparatus of claim 9, wherein the encapsulation layer includes a particle cover layer.

14. The apparatus of claim 9, wherein the camera includes a line scan camera and displays a color image.

15. The apparatus of claim 9, further comprising: an alignment camera configured to align the encapsulation layer with the optical inspection assembly.

16. The apparatus of claim 9, wherein the inspection apparatus is configured to adjust focus of the optical inspection assembly with respect to the encapsulation layer when the optical inspection assembly moves along an inspection region of the encapsulation layer.

17. The apparatus of claim 9, further comprising: a lens having a pixel number corresponding to a number of pixels of the camera.

18. The apparatus of claim 9, wherein the defect detector converts the intensity of the light into the thickness of the encapsulation layer corresponding to the intensity of the light.

19. The apparatus of claim 9, wherein the inspection apparatus is disposed prior to a device for post-processes of the organic light-emitting panel.

20. The method of claim 1, wherein the encapsulation layer of the organic light-emitting panel includes a layer of an organic material.

21. The method of claim 20, wherein the organic material comprises at least one of: silicon oxycarbide (SiOCz), acrylic resin, and epoxy resin.

* * * * *